United States Patent [19]

Barrows

[11] 4,343,931
[45] Aug. 10, 1982

[54] SYNTHETIC ABSORBABLE SURGICAL DEVICES OF POLY(ESTERAMIDES)

[75] Inventor: Thomas H. Barrows, Cottage Grove, Minn.

[73] Assignee: Minnesota Mining and Manufacturing Company, St. Paul, Minn.

[21] Appl. No.: 103,915

[22] Filed: Dec. 17, 1979

[51] Int. Cl.³ .............................................. C08G 63/68
[52] U.S. Cl. .................................. 528/291; 128/334 R; 128/335.5; 528/281; 528/285; 528/335; 528/336; 528/341; 528/361; 528/367; 528/370; 523/113
[58] Field of Search ................ 528/291, 361, 367, 370

[56] References Cited

U.S. PATENT DOCUMENTS

| | | | |
|---|---|---|---|
| Re. 30,170 | 12/1979 | Goodman et al. | 528/327 |
| 2,954,364 | 9/1960 | Coleman et al. | 528/291 |
| 3,025,323 | 3/1962 | Rose et al. | 260/561 |
| 3,049,518 | 8/1962 | Stephens | 528/348 |
| 3,063,967 | 11/1962 | Schultz | 528/354 |
| 3,063,968 | 11/1962 | Schultz | 528/354 |
| 3,094,511 | 6/1963 | Hill et al. | 528/348 |
| 3,297,033 | 1/1967 | Schmitt et al. | 128/335.5 |
| 3,475,385 | 10/1969 | Goodman et al. | 528/310 |
| 3,636,956 | 11/1972 | Schneider | 128/335.5 |
| 3,817,932 | 6/1974 | Albers et al. | 528/291 |
| 3,839,297 | 10/1974 | Wasserman et al. | 528/354 |
| 3,883,901 | 5/1975 | Coquard et al. | 3/1 |
| 4,032,993 | 7/1977 | Coquard et al. | 3/1 |
| 4,052,988 | 10/1977 | Doddi et al. | 128/335.5 |
| 4,209,607 | 6/1980 | Shalaby et al. | 528/291 |

FOREIGN PATENT DOCUMENTS 2236949  7/1972  Fed. Rep. of Germany ...... 528/291

OTHER PUBLICATIONS

Encyclopedia of Polymer Science and Technology, vol. 10 (1969), pp. 347-349, 483-491.

*Primary Examiner*—Harold D. Anderson
*Attorney, Agent, or Firm*—Cruzan Alexander; Donald M. Sell; Lorraine R. Sherman

[57] ABSTRACT

A body absorbable polymeric material for implantation which is a condensation product of reacting a diamine with lactic or glycolic acid to form a diamidediol which is then reacted with a bischloroformate or a compound selected from the group consisting of dicarboxylic acids, methyl and ethyl esters of dicarboxylic acids, diacidchlorides, and anhydrides of a dicarboxylic acid.

12 Claims, 1 Drawing Figure

SYNTHETIC ABSORBABLE SURGICAL DEVICES OF POLY(ESTERAMIDES)

Figure 1:
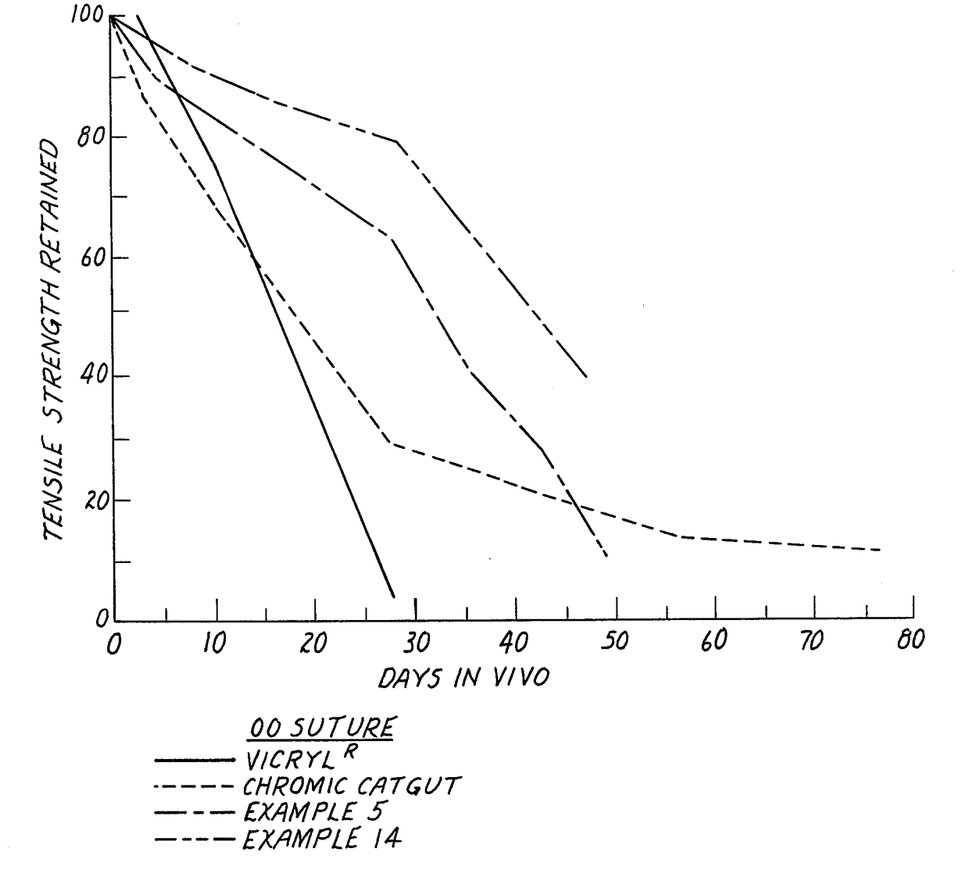

This invention relates to new and useful bioabsorbable polymeric materials derived from reacting diamidediols with a dicarboxylic acid or a bischloroformate and to the methods for the preparation of such polymeric materials.

It has become common practice in human and animal surgery to utilize various augmentation devices to restore living tissues or repair various organs. These surgical augmentation devices are usually placed in position either temporarily or permanently. One such augmentation device is a surgical suture.

Surgical sutures were originally fabricated from naturally occurring substances. Such naturally occurring materials include silk and catgut or collagen. Although these naturally occurring materials are still in widespread use, modern synthetic fibers made of nylons, polyesters, polyolefins and the like are steadily displacing the use of these natural materials for a variety of reasons. For example, synthetic fibers generally cause for less adverse tissue reactions and are less likely to potentiate infection than either silk or catgut.

In the case of the surgical suture which is placed for temporary purposes, the suture should be made so that it is absorbed by the body after serving its function in the augmentation or wound repair process. Absorbed is used herein to mean that a substantial portion of the polymer is metabolized by the body and ultimately eliminated therefrom.

Several absorbable sutures are presently known to the art. For example, see U.S. Pat. Nos. 3,636,956 and 3,839,297. The sutures disclosed in the aforementioned patents consist of an extrusion of a polylactide polymer which includes a copolymer of L(—)lactide with up to 35 mole percent of glycolide. While multifilament sutures manufactured from polymers of lactide and glycolide fulfill the requirements of a suture to a large degree, monofilament sutures of these materials are considerably less flexible than catgut and these synthetic sutures are accordingly generally limited to a multifilament, braided construction. Braided sutures have the disadvantages of causing trauma upon being pulled through tissue due to a sawing action, a.k.a. tissue drag. Sutures of glycolide polymers are also not suitable for sterilization by radiation without suffering severe degradation of physical properties.

Another serious disadvantage of the polyglycolide sutures is the fact that strength loss in vivo proceeds at a rapid rate. Such fibers are known to possess virtually no strength at three to four weeks. While this is not a problem in some applications, the polyglycolide sutures are contraindicated where extended approximation is advisable.

The present invention provides synthetic absorbable sutures having a high degree of softness and flexibility while at the same time allowing the sutures to be used in monofilament form. The sutures can also be sterilized with gamma radiation (e.g., radiation from cobalt 60) without serious loss of suture strength. It is accordingly an object of the present invention to provide synthetic absorbable sutures having unique and desirable properties not available with the sutures of the prior art.

The synthetic absorbable sutures of the present invention are prepared from a polymeric material having a plurality of units of the general formula:

wherein
R¹ is hydrogen or methyl;
R³ and R⁵ may be identical or different and are selected from the group consisting of the following which may be linear or branched, alkylene, alkylene having 1 or 2 nonadjacent catenary oxygen or sulfur atoms, alkenylene, cycloalkylene and arylene; and having up to 25 carbon atoms in the cyclic compounds and from 2 to 25 carbon atoms in the non-cyclic;
R² and R⁴ are hydrogen or alkyl having 1 to 4 carbon atoms or R² and R⁴ together are linear or branched akylene having one to four carbons forming with N—R³—N a heterocyclic group having 5 or 6 ring atoms; and
a and b are independently zero or one.

The polymeric materials of the present invention may be prepared by utilizing a process which involves reacting a diamine with lactic or glycolic acid to form a diamidediol. The resulting diamidediol is then reacted with a dicarboxylic acid or derivative (e.g. diacid chloride diester or anhydrides) or a bischloroformate to form the polymeric material which can then be processed to the desired configuration.

The body absorbable surgical materials of the present invention are comprised of a polymer of the general formula:

in which
R¹ is hydrogen or methyl;
R³ and R⁵ may be identical or different and are selected from the group consisting of the following, which may be linear or branched, alkylene, alkylene having 1 or 2 nonadjacent catenary oxygen or sulfur atoms, alkenylene, cycloalkylene and arylene; having up to 25 carbon atoms in the cyclic compounds and from 2 to 25 carbon atoms in the non-cyclic compounds;
R² and R⁴ are hydrogen or alkyl having 1 to 4 carbon atoms or R² and R⁴ together are linear or branched alkylene having one to four carbons forming with N—R³—N a heterocyclic group having 5 or 6 ring atoms;
a and b are independently zero or one; and
n having an average value from about 10 to about 100.

In order to obtain the regular sequence shown, it is desirable to first form the amide linkages prior to polymerization. This can be accomplished by combining about two moles of glycolic or lactic acid with about one mole of a diamine and heating at a temperature between 150° to 220° C. until distillation of water is complete. Alternatively, combination of hydroxy acid and diamine will produce a salt which can be purified by recrystallization and then subjected to the above condensation. In either case, a high yield of diamidediol is obtained which can be purified by recrystallization.

Diamidediols useful in synthesizing polymers of this invention can be prepared by the above methods from diamines such as 1,2-ethanediamine; 1,3-propanediamine; 1,3-(2-methylpropane)diamine; 1,3-(2,2-dimethylpropane)-diamine; 1,2-(1,2-dimethylethane)diamine; 1,4-butanediamine; 1,5-pentanediamine; 1,6-hexanediamine; 1,7-heptanediamine; 1,8-octanediamine; 1,9-nonanediamine; 1,10-decanediamine; 1,11-undecanediamine; 1,12-dodecanediamine; 1,13-tridecanediamine; 1,14-tetradecanediamine; 1,15-pentadecanediamine; 1,16-hexadecanediamine; 3-oxapentane-1,5-diamine; 4-oxaheptane-1,7-diamine; 5-oxanonane-1,9-diamine; 6-oxaundecane-1,11-diamine; 7-oxatridecane-1,13-diamine; 8-oxapentadecane-1,15-diamine; 9-oxaheptadecane-1,17-diamine; 10-oxanonadecane-1,19-diamine; 11-oxaheneicosane-1,21-diamine, 12-oxatricosane-1,23-diamine; 13-oxapentacosane-1,25-diamine; 4,9-dioxadodecane-1,12-diamine; 3,6-dioxaoctane-1,8-diamine and other analogs of oxa-aliphatic diamines and the corresponding thia-aliphatic diamines; cyclohexane-1,14-diamine; cyclohexane-1,3-diamine; cyclohexane-1,2-diamine; 1,4-bis(aminomethyl)cyclohexane; 1,3-bis-(aminomethyl)cyclohexane; 1,4-bis(2-aminoethyl)cyclohexane; 1,4-bis(3-aminopropyl)cyclohexane; bis(4-aminocyclohexyl)methane; p-phenylenediamine; o-phenylenediamine; m-phenylenediamine; p-xylylene-$\alpha,\alpha$-diamine and other aromatic diamines; piperazine; 4,4'-trimethylenedipiperidine; 4,4'-bipiperidine; N,N'-bis(3-aminopropyl)piperazine; 2,5-dimethylpiperazine; 2,6-dimethylpiperazine; 2-methylpiperazine; imidazolidine; 2-methylimidazolidine; 4,5-dimethylimidazolidine.

In the preferred body absorbable polymeric material, it is preferred that the diamidediols be a mixture of 1,12-di(hydroxyacetamido)-4,9-dioxadodecane and 1,12-di(hydroxyacetamido)dodecane, with groups $R^1$, $R^2$, $R^3$, and $R^4$ being formed by the removal of the elements of water in the condensation of glycolic acid with 4,-9, -dioxa-1,12-docecanediamine and 1,12-dodecanediamine.

Synthesis of the body absorbable polymer of the present invention can be accomplished by any of a number of well known techniques. For example, the diamidediol can be combined with an equimolar amount of one or more dicarboxylic acids or dicarboxylic acid methyl esters and appropriate esterification catalyst, e.g. $Sb_2O_3$, and heated with stirring under nitrogen at temperatures of 150° to 250° C. for 10 to 100 hours with 175° to 200° C. for 20 to 40 hours being preferred.

A preferred method of preparing polymer consists of dissolving the diamidediol in a solvent which is nonreactive with acid chlorides and has a boiling point of 100° C. or higher, heating the mixture to reflux, and rapidly adding an equimolar amount of a diacid chloride with vigorous mechanical mixing (e.g. motor driven paddle), separating the polymer from solvent and drying the polymer at temperatures below the melting point of the polymer. Suitable solvents include methylchloroacetate, chlorobenzene 1,1,2-trichloroethane or 1,4-dioxane. The preferred solvent for uses with a diacid chloride is chlorobenzene.

The preferred method has the advantages of not requiring catalyst, of yielding product in a relatively short period of time, and producing high molecular weight polymer in a granular, easy-to-manipulate form. In addition, moisture which would otherwise react with the acid chloride can be readily excluded from the system by azeotropic distillation prior to addition of the diacid chloride. Polymer prepared by this method can be further improved with respect to increasing the molecular weight by heating for several days under partial vacuum with a stream of dry nitrogen passing over the polymer at temperatures that are 10° to 50° C. below the polymer melting temperature.

Dicarboxylic acid chlorides and the diacid dimethyl or diethyl esters of dicarboxylic acids useful in the synthesis of polymers by the above methods include those derived from the dicarboxylic acids listed below. In addition, the free acids can also be used. The term "dicarboxylic acid" as used herein includes dicarboxylic acids, their methyl and ethyl esters, their acid chlorides and anhydrides. They are, for example, oxalic acid; malonic acid; succinic acid; 2,3-dimethylsuccinic acid; glutaric acid; 3,3-dimethylglutaric acid; 3-methyladipic acid; adipic acid; pimelic acid; suberic acid; azelaic acid; sebacic acid; 1,9-nonanedicarboxylic acid; 1,10-decanedicarboxylic acid; 1,11-undecanedicarboxylic acid; 1,12-dodecanedicarboxylic acid; 1,13-tridecanedicarboxylic acid; 1,14-tetradecanedicarboxylic acid; 1,15-pentadecanedicarboxylic acid; 1,16-hexadecanedicarboxylic acid; maleic acid; trans-$\beta$-hydromuconic acid; fumaric acid; diglycolic acid; 3,3'-oxydipropionic acid; 4,4'-oxydibutyric acid; 5,5'-oxydivaleric acid; 6,6'-oxydicaproic acid; 8,8'-oxydicaprylic acid; 6-oxaundecanedioic acid; 5-oxaazelaic acid; 5-oxasebacic acid; 5-oxaundecanedioic acid; 5-oxadodecanedioic acid; 5-oxatetradecanedioic acid; 5-oxahexadecanedioic acid; 6-oxadodecanedioic acid; 6-oxatridecanedioic acid; 6-oxapentadecanedioic acid; 6-oxaheptadecanedioic acid; 7-oxapentadecanedioic acid; 10-oxanonadecanedioic acid and other oxa-aliphatic dicarboxylic acids; phthalic acid; isophthalic acid; terephthalic acid and other aromatic dicarboxylic acids; 1,2-cyclobutanedicarboxylic acid; 1,4-cyclohexane-dicarboxylic acid. In the preferred body absorbable polymeric material, $R^5$ is preferably ethylene being formed by the removal of the chloride from succinyl chloride.

Polymers can also be prepared by reaction of the diamidediols with bischloroformates. The bischloroformates, in turn, can be prepared by reacting a dihydroxy compound with excess phosgene gas in the condensed phase or in solution (see *Preparative Methods of Polymer Chemistry*, 2nd ed., Sorenson and Campbell, Interscience Pub (1968), p.123). Dihydroxy compounds that can be used include, for example, the previously mentioned diamidediols; ethylene glycol; 1,3-propanediol; 1,4-butanediol; 1,5-pentanediol; 1,6-hexanediol; 1,7-heptanediol; 1,8-octanediol; 1,9-nonanediol; 1,10-decanediol; 1,11-undecanediol; 1,12-dodecanediol; 1,13-tridecanediol; 1,14-tetradecanediol; 1,15-pentadecanediol; 1,16-hexadecanediol; oxaaliphatic diols and poly(ethyleneoxy)diols of various molecular weights.

The polymeric materials of this invention can be fabricated into films and fibers by melt extrusion. When the films are fabricated into fibers, it is preferred that n of the general formula have an average value from about 30 to about 50. Such fibers have been implanted subcutaneously in mice and have been found to be non-irritating and compatible with the living tissue over the time span of many months. After approximately eight months, a substantial amount of the polymer is absorbed by the living tissue.

The polymers of the present invention are also useful in the manufacture of cast and/or extruded films and molded solid surgical aids. Thus, cylindrical pins, screws, reinforcing plates, etc., may be machined from the cast or molded polymer having the aforementioned in vivo absorption characteristics.

The preparation of the body absorbable polymeric material of the present invention may be further illustrated by reference to the following examples:

EXAMPLE 1

1. Synthesis of 1,12-di(hydroxyacetamido)dodecane

Two moles of vacuum redistilled 1,12-dodecanediamine (400 g) were dissolved in 5 liters of isopropyl alcohol in a 6 liter stainless steel beaker and four moles of glycolic acid (304 g) were added carefully in small portions with stirring. The resultant solution was covered with aluminum foil and allowed to cool gradually to room temperature whereupon formation of a white crystalline solid occurred. The crystals were collected on a large Buchner funnel, rinsed with isopropanol, and air dried yielding 647 g (92%), m.p. 94°–97° C.

The solid was placed in a 5 liter round bottom 3-neck flask and heated in a large oil bath with overhead stirring. A stream of dry nitrogen was passed into the system and through the attached distillation apparatus. The melted solid was heated to 190° C. at which temperature vigorous distillation of water occurred. After 4 hours evolution of water had subsided completely and the liquid was poured into metal pans where it rapidly solidifed. The product was recrystallized from 6 liters of absolute methanol to yield 530 g (84%) of lustrous white crystals; m.p. 127°–130° C.; infrared (Nujol) 1650 $cm^{-1}$, 3250 $cm^{-1}$; proton nuclear magnetic resonance (DMSO-$d_6$/TMS, 100 MHz) $\delta 1.27$ (singlet, 20 protons), $\delta 3.13$ (quartet, 4 protons), $\delta 3.82$ (doublet, 4 protons), $\delta 5.47$ (triplet, 2 protons), and $\delta 7.73$ (broad triplet, 2 protons).

2. Synthesis of poly[dodecane-1,12,di(carbonyloxy)-dodecane-1,12-di(amidocarbonylmethylene)].

Exactly 486.3 g (1.54 moles) of 1,12-di(hydroxyacetamido)dodecane and 397.0 g (1.54 moles) of 1,12-dodecanedicarboxylic acid were melted together in a 2 liter glass resin flask heated in an oil bath. Overhead stirring of the molten mixture was commenced and 0.8 g of Irganox 1010 (a phenolic antioxidant available from Ciba-Giegy) added. Dry nitrogen was admitted through a tube reaching below the surface of the liquid. The mixture was heated at 175° C. for 20 hours during which time distillation of water occurred. Antimony trioxide (0.8 g) was added and heating and stirring were continued for an additional 16 hours at 200° C. The viscous, light brown colored product was poured out and allowed to solidify. The solid was dissolved in 15 liters of boiling isopropanol and the solution allowed to cool to 30° C. at which temperature the precipitated solid was collected and dried to yield 525 g of powder; inherent viscosity 0.26 (0.5% in 1,1,1-trifluoroethanol (TFE) at 30° C.); differential thermal analysis, Tg= −1° to +20° C., Tm=93° C.

3. In vivo evaluation.

The above polymer was melt extruded in a ⅜ inch Brabender Extruder equipped with 30:1 L/D ratio general purpose screw and oriented at a temperature above its glass transition temperature by drawing at a ratio between about 4 to 1 and 10 to 1 to produce uniform fiber with a tenacity of 2.5 g/denier. The fiber was cut into 20 cm lengths which were alternately assigned to control and experimental groups. All fiber was handled the same with respect to ethylene oxide sterilization and drying. The experimental set of fibers were surgically implanted subcutaneously in mice. The mice were necropsied at various time intervals and the tensile strength of recovered fiber measured after drying and compared with control samples. The data recorded in Table 1 was obtained by averaging 8 to 10 individual values recorded at each time period.

TABLE 1

| Days Post Implantation | Tensile Strength Retained |
|---|---|
| 5 | 46.6% |
| 7 | 28.0% |
| 14 | 12.3% |

Additional fiber implanted mice were necropsied at monthly intervals. After two months the fibers possessed virtually no physical integrity, were broken into small pieces approximately 1 to 2 mm in length, and were encapsulated. By six months only a trace of the polymer could be detected visually, the majority having been completely absorbed. In all of these evaluations there was no visible reaction to the surrounding tissue and no evidence of toxicity.

EXAMPLE 2

Alternate synthesis of poly[dodecane-1,12-di(carbonyloxy)dodecane-1,12-di(amidocarbonylmethylene)].

Dimethyl-1,12-dodecanedicarboxylate (19.72 g, 0.069 mole) and 1,12-di(hydroxyacetamido)dodecane (21.79 g, 0.069 mole) prepared according to the procedure in Example 1 were placed in a 250 ml round bottom 3-neck flask and heated in an oil bath with overhead stirring. About 10 mg of Irganox 1010, and zinc acetate (about 10 mg) were added and the mixture heated to 185° C. with dry nitrogen passing over the reactants and through the attached distillation apparatus. Heating and stirring were continued for 20 hours at 170°–185° C. Antimony trioxide (about 10 mg) was added and the temperature maintained at 190°–200° C. for an additional 20 hours. During this time the melt increased in viscosity and high vacuum was applied intermittently. The dark brown product was allowed to cool and was then dissolved in hot isopropyl alcohol (1 liter). The isopropyl alcohol solution was allowed to cool to 30° C. at which temperature the precipitated solid was collected and dried to yield 30.1 g of powder; inherent viscosity 0.27 (0.5% in TFE at 30° C.); differential thermal analysis, Tg= +3° to +24° C., Tm=117° C.

The powdered polymer was placed in a glass U tube and heated in an oil bath for 60 hours at 97° C. During this time a slow stream of dry nitrogen was passed through the polymer which remained in the solid state. As a result of this treatment the inherent viscosity increased significantly (0.36). Filaments pulled from the melted polymer were easily cold drawn by hand to yield tenacious fibers.

EXAMPLE 3

1. Synthesis of poly[oxysebacoyloxydodecane 1,12-di(amidocarbonylmethylene)].

Exactly 404.7 g (1.28 moles) of 1,12-di(hydroxyacetamido(oxydodecane prepared according to the procedure in Example 1 and 258.5 g (1.28 moles) of sebacic acid were melted together in a 2 liter glass resin flask heated in an oil bath. Overhead stirring was commenced and 0.6 g of Irganox 1010 antioxidant added. Dry nitrogen was admitted through a tube reaching below the surface of the liquid. The mixture was heated at 175° C. for 20 hours during which time distillation of water occurred. 0.6 g of antimony trioxide was added and heating and stirring continued for an additional 20 hours at 190° C. Nitrogen flow was discontinued, the system was placed under vacuum of about 0.1 Torr, and heating and stirring continued for 4 hours at 210° C. The reaction was then discontinued and the viscous, brown liquid poured into a metal pan where it solidified into a hard, tough solid. The solid was dissolved in 3 liters of boiling isopropanol and the solution poured slowly into 4 liters of acetone with vigorous stirring. The resultant precipitate was collected and dried to yield 430 g of powder; inherent viscosity 0.32 (0.5% in TFE at 30° C.); differential analysis, Tg= −10° to +9° C., Tm=50° C.

2. In vivo evaluation.

The above polymer was melt extruded and oriented as in Example 1 to produce uniform fiber with a tenacity of 0.82 g/denier. The fiber was implanted in mice as described in Example 1. The strength loss results are shown in Table 2.

TABLE 2

| Days Post Implantation | Tensile Strength Retained |
|---|---|
| 3 | 61.4% |
| 10 | 18.8% |

The implantation site in each of the mice showed no visible inflammation or other evidence of an adverse reaction toward the polymer.

EXAMPLE 4

1. Synthesis of 1,10-di(hydroxyacetamido)decane.

1,10-Decanediamine (10 g, 0.058 mole) was dissolved in 150 ml of boiling isopropanol and solid glycolic acid (8.8 g, 0.116 mole) added portion-wise with stirring. An oil that separated from the cooled solution rapidly crystallized upon scratching. Recrystallization from isopropanol yielded white crystals (16.3 g, 87% yield, m.p. 57°-62° C.).

The 1,10-decanediammonium glycolate was placed in a 3-neck 100 ml round bottom flask and heated in an oil bath with magnetic stirring. Dry nitrogen was passed over the melted solid and through the attached distillation apparatus. Distillation of water occurred at 150° C. After 4 hours at 150°-165° C., no further evolution of water could be detected and the liquid was poured into a dish where it rapidly solidified. Recrystallization from methanol gave 10.7 g (74%) of white crystals; m.p. 120°-122° C.

2. Synthesis of poly[decane-1,10-di(carbonyloxy)decane-1,10-di(amidocarbonylmethylene)].

Exactly 9.50 g (0.033 mole) of 1,10-di(hydroxyacetamido)decane and 7.66 g (0.033 mole) of 1,10-decanedicarboxylic acid were placed in a 100 ml round bottom flask and heated in an oil bath with overhead stirring. Irganox 1010 antioxidant (about 5 mg) was added and the mixture heated to 170° C. with dry nitrogen passing over the reactants and through the attached distillation apparatus. Heating and stirring were continued overnight (16 hours) at 170° C. Antimony trioxide (about 5 mg) was added and the temperature increased to 190°-210° C. for 8 hours. During this time the melt became rather viscous and a vacuum of about 0.1 Torr was applied intermittently. The melt was allowed to cool completely overnight and was then reheated to 210° C. for 2 hours followed by an additional 30 minutes under vaccum. The viscous, amber colored product was poured onto a metal surface where it cooled to form a tough solid; inherent viscosity 0.26 (0.5% in TFE at 30° C.); differential thermal analysis, Tg= −8° to +2° C., Tm=51° C. Filaments pulled from the melted polymer were easily cold drawn by hand to yield tenacious fibers.

EXAMPLE 5

1. Synthesis of poly[oxysuccinoyloxydodecane-1,12-di(amidocarbonylmethylene)].

Exactly 390.4 g (1.235 moles) of 1,12-di(hydroxyacetamido)dodecane prepared according to the procedure in Example 1 and 1 kg of chlorobenzene were placed in a 3 liter resin flask and heated in an oil bath with overhead stirring. The solid dissolved and approximately 200 ml of chlorobenzene was distilled from the solution. The solution was allowed to cool to 120° C. and the distillation apparatus was replaced with a reflux condenser connected to gas washing bottles, the first empty and the second filled with water. Vacuum redistilled succinyl chloride (191.5 g, 1.235 moles) was added cautiously through an addition funnel to the solution while stirring at approximately 300 rpm. The exothermic reaction was accompanied by vigorous evolution of hydrogen chloride gas. Approximately 20 minutes after addition of succinyl chloride, the solution became viscous and the polymer solidified and separated from the solution. The mixture was refluxed with stirring for an additional 2 hours during which time the evolution of hydrogen chloride subsided. The chlorobenzene was removed by distillation under reduced pressure to yield 490 g of product; inherent viscosity 0.45 (0.5% in TFE at 30° C.); differential thermal analysis, Tg= +16° to +48° C., Tm=160° C.

The product was placed in a 3-neck flask and heated in an oil bath for 48 hours at 130° C. During this time a slow stream of dry nitrogen was passed through the polymer which remained in the solid state. As a result of this treatment the inherent viscosity increased significantly (0.81).

2. In vivo evaluation.

The above polymer was melt extruded and oriented as in Example 1 to produce uniform fiber corresponding to U.S.P. suture size number 00 with a tenacity of 2.4 g/denier. Two commercial U.S.P. number 00 absorbable sutures, Vicryl ® (Ethicon, Inc.) and chromic catgut (Ethicon, Inc.), were purchased and included in the evaluation. The in vivo fiber strength retention data was obtained as described in Example 1 and is shown in the accompanying figure.

The strength loss profile of fiber produced in this example illustrates that this polymer should be useful clinically where approximation of healing tissue is required for a longer period of time than can presently be achieved with currently available absorbable sutures.

The implantation site revealed no evidence of irritation or incompatibility in each of the necropsies involving the above polymer. This was not the case with chromic catgut, however, which produced inflammatory reactions varying from slight to massive.

EXAMPLE 6

1. Synthesis of 4,4'-methylenebis(hydroxyacetamidocyclohexane).

4,4'-Methylenebis(cyclohexylamine) (56.5 g, 0.27 mole) was dissolved in hot isopropanol (500 ml) and glycolic acid (40.9 g, 0.54 mole) added portion-wise with stirring. Upon cooling, a white gummy solid separated which was isolated by decantation and redissolved in a small volume of ethanol. Crystallization produced a white crystalline, deliquescent solid; m.p. 96°–102° C. Thorough drying under vacuum increased the melting point (m.p. 149°–151° C.) and reduced the deliquescence.

The solid was placed in a 250 ml round bottom flask and heated in an oil bath with stirring. Distillation of water occurred at 150° C. and the temperature was increased to 175° C. After stirring at 175° C. for 3 hours the melt suddenly resolidified into a white crystalline mass. The solid was recrystallized from a mixture of ethanol and methanol to yield lustrous, white crystals, m.p. 208°–211° C.; infrared (Nujol), 1630 cm$^{-1}$, 3250 cm$^{-1}$; proton nuclear magnetic resonance (CDCl$_3$/TMS, 100 MHz), $\delta$0.6–1.5 (complex multiplet, 12 protons), $\delta$1.5–1.8 (doublet, 8 protons), $\delta$3.50 (broad singlet, 2 protons), $\delta$3.75 (doublet, 4 protons), $\delta$5.35 (triplet, 2 protons), $\delta$7.37 (doublet, 2 protons).

2. Alternate synthesis of 4,4'-methylenebis(hydroxyacetamidocyclohexane).

4,4'-Methylenebis(cyclohexylamine) (25 g, 0.12 mole) and glycolic acid (18.2 g, 0.24 mole) were combined in a 250 ml round bottom flask heated in an oil bath. The solids were melted together with mixing and heated to 175° C. whereupon distillation of water occurred. After heating for 3 hours the evolution of water subsided and crystallization commenced. The solid was removed and recrystallized from methanol to yield 34 g (87%) of lustrous white needles; m.p. 208°–212° C.

3. Synthesis of poly[decane-1,10-di(carbonyloxy)-dicyclohexylmethane-4,4'-di(amidocarbonylmethylene)].

Exactly 1.748 g (0.0065 mole) of 1,10-decanedicarbonyl chloride was placed in a 100 ml round bottom flask and dissolved in chlorobenzene (20 ml). 4,4'-Methylenebis(hydroxyacetamidocyclohexane) (2.120 g, 0.0065 mole) was added and the mixture heated to reflux with stirring. Vigorous evolution of hydrogen chloride occurred, and after refluxing for approximately 30 minutes the mixture became a clear, colorless solution.

Refluxing was continued for 2 hours and the solution then allowed to cool whereupon precipitation occurred. The precipitate was collected by filtration and dried under vacuum to give a white powder; inherent viscosity (0.5% in TFE at 30° C.) of 0.35; differential thermal analysis, Tg= +75° to +85° C., Tm=185° C. Filaments pulled from the melted polymer were easily cold drawn by hand to give tenacious fibers.

EXAMPLE 7

Synthesis of poly[ethane-1,2,-di(oxycarbonyloxy)-dicyclohexylmethane-4,4'-di(amidocarbonylmethylene)].

Exactly 5.643 g (0.0301 mole) of vacuum redistilled ethylene bischloroformate were placed in a 50 ml round bottom flask and 20 ml of chlorobenzene added followed by 9.837 g (0.0301 mole) of 4,4'-methylenebis(hydroxyacetamidocyclohexane) prepared according to the procedure in Example 6. The mixture was heated in an oil bath to 130° C. with rapid magnetic stirring. Vigorous evolution of hydrogen chloride gas occurred and the mixture turned dark yellow in color. After refluxing the mixture for 2 hours, the solid was collected by filtration and dried under vacuum to yield a light tan colored powder; inherent viscosity 0.09 (0.5% in TFE at 30° C.); infrared (Nujol), 1650 cm$^{-1}$, 1750 cm$^{-1}$; differential thermal analysis, Tg= +70° to +84° C., Tm=180° C. with decomposition.

EXAMPLE 8

1. Synthesis of trans-1,4-cyclohexanebis(hydroxyacetamidomethyl).

Glycolic acid (313 g, 4.12 moles) was dissolved in 2 liter of absolute methanol and a methanolic solution of 1,4-cyclohexanebis(methylamine) (291 g, 2.05 moles, approximately 20% cis and 80% trans isomers) added carefully with stirring. The hot solution was boiled for 3 to 5 minutes and then cooled slowly to 4° C. whereupon crystallization occurred. The white, crystalline product was collected on a Buchner funnel, rinsed with methanol, and dried under vacuum at 60° C. to yield 541 g (89.5%); m.p. 199°–201° C.

The glycolic acid salt was placed in a 3 liter 3-neck round bottom flask heated in an oil bath with mechanical stirring. Dry nitrogen was passed into the system and through the attached distillation apparatus. Upon heating to 210° C., vigorous distillation of water occurred and subsided completely after 45 minutes. 73.8 g (99.5%) of water were collected. The solidified product was dissolved in 6 liters of hot absolute ethanol and allowed to cool slowly to room temperature whereupon crystallization occurred. The clusters of long, pale yellow colored needles which formed were collected and dried to yield 273 g (51.4%); m.p. 182°–186° C.; infrared (Nujol), 1625 cm$^{-1}$, 3270 cm$^{-1}$; proton nuclear magnetic resonance (DMSO-d$_6$/TMS, 100 MHz), $\delta$0.6–1.9 (complex multiplet, 10 protons), $\delta$2.98 (triplet, 4 protons), $\delta$3.83 (doublet, 4 protons), $\delta$5.44 (triplet, 2 protons), $\delta$7.67 (triplet, 2 protons).

The filtrate was concentrated to a volume of 2 liters and cooled to −20° C. whereupon a powdery white solid appeared. The solid was collected and dried to yield 104 g (19.6%); m.p. 136°–142° C. The proton nuclear magnetic resonance spectrum for this material is essentially the same as above except that the multiplet at $\delta$3.0 is more complex and the multiplet at $\delta$0.6–1.9 is partially replaced by a singlet occurring at $\delta$1.35. It is estimated that this lower melting fraction is approximately 40% trans and 60% cis isomers of the desired product whereas the higher melting major fraction is virtually pure trans isomer. It is believed that fractional crystallization is possible due to the fact that the cis isomer can form intramolecular hydrogen bonds whereas the trans isomer cannot.

2. Synthesis of poly[trans-oxysebacoyloxycyclohexane-1,4-di(methylene amidocarbonylmethylene)].

186.0 g (0.721 mole) of trans-1,4-cyclohexanebis(hydroxyacetamidomethyl) were placed in a 3 liter 3-neck round bottom flask and 800 g of chlorobenzene added. The mixture was heated with overhead stirring and approximately 150 ml of chlorobenzene distilled from the solution. The distillation apparatus was then replaced with a reflux condenser as in Example 5. Vacuum redistilled sebacoyl chloride (172.3 g, 0.721 mole) was added carefully through an addition funnel with rapid stirring. Vigorous evolution of hydrogen chloride gas occurred and the product separated as a granular solid. The mixture was refluxed for 2 hours during which time evolution of hydrogen chloride gas subsided. Filtration while hot and drying under vacuum yielded 208 g of powder; inherent viscosity 0.60 (0.5% in TFE at 30° C.); differential thermal analysis, Tg=+50° to +57° C., Tm=180° C.

The polymer was melt extruded and oriented as in Example 1 to produce uniform fiber with a tenacity of 1.70 g/denier.

EXAMPLE 9

1. Synthesis of N,N'-di(hydroxyacetyl)piperazine.

Piperazine hexahydrate (17.5 g, 0.090 mole) was dissolved in 1 liter of absolute methanol and solid glycolic acid (13.7 g, 0.180 mole) added with stirring. The solution was boiled for a few minutes and then allowed to cool slowly. Crystallization produced long, white needles which were collected and dried under vacuum to give 16.3 g (76%); m.p. 169°–173° C. The product was placed in a 100 ml round bottom flask and heated in an oil bath with magnetic stirring. A stream of dry nitrogen was passed through the system and the temperature maintained at 180°–190° C. for 3 hours. After distillation of water subsided, the liquid was solidified and recrystallized from 1 liter of absolute ethanol to give a white powder; m.p. 187°–190° C.; infrared (Nujol), 1625 $cm^{-1}$, 3250 $cm^{-1}$; proton nuclear magnetic resonance (DMSO-$d_6$/TMS, 100 MHz), $\delta 3.43$ (singlet, 8 protons), $\delta 4.12$ (singlet, 4 protons), $\delta 4.63$ (broad singlet, 2 protons).

2. Synthesis of poly(oxysuccinoyloxy)piperazine-N,N'-di(carbonylmethylene).

N,N'-di(hydroxyacetyl)piperazine (2.70 g, 0.0133 mole) was placed in a 50 ml round bottom flask and 15 ml of chlorobenzene added. The mixture was stirred magnetically and vacuum redistilled succinyl chloride (2.07 g, 0.0133 mole) added. The mixture was heated in an oil bath at 120°–130° C. for 3 hours during which time evolution of hydrogen chloride gas occurred. The product was collected by filtration and dried under vacuum to yield a tan colored powder; inherent viscosity 0.14 (0.5% in TFE at 30° C.); differential thermal analysis, Tg=+55° to +75° C., Tm=200° C. with decomposition.

EXAMPLE 10

1. Synthesis of 1,12-di(hydroxyacetamido)-4,9-dioxadodecane.

4,9-Dioxadodecane-1,12-diamine (22.8 g, 0.112 mole) was placed in a 250 ml round bottom flask and glycolic acid (17.0 g, 0.224 mole) added portion-wise with stirring and cooling. The resultant liquid was heated in an oil bath to 185° C. whereupon distillation of water occurred. Heating was continued at 185° to 195° C. for 2 hours after which time distillation of water subsided and the liquid was poured into a crystallization dish. The resultant oil slowly crystallized in the form of large white clusters; yield 35.5 g (99.3%); m.p. 67°–71° C. The solid was recrystallized from cold absolute methanol to give a white, crystalline product; m.p. 74°–77° C.; infrared (Nujol), 1120 $cm^{-1}$, 1625 $cm^{-1}$, 3250 $cm^{-1}$; proton nuclear magnetic resonance (CDCl$_3$/TMS, 100 MHz), $\delta 1.55$–1.95 (complex multiplet, 8 protons), $\delta 3.30$–3.65 (complex multiplet, 12 protons), $\delta 4.03$ (singlet, 4 protons), $\delta 4.98$ (broad singlet, 2 protons), $\delta 7.51$ (broad triplet, 2 protons).

2. Synthesis of poly[oxysuccinoyloxy-4,9-dioxadodecane-1,12-di(amidocarbonylmethylene)].

Redistilled succinyl chloride (5.437 g, 0.035 mole) was placed in a 100 ml round bottom flask and diluted with chlorobenzene (40 ml). The solution was stirred magnetically and 1,12-di(hydroxyacetamido)-4,9-dioxadodecane (11.224 g, 0.035 mole) added. The mixture was heated in an oil bath to 50° C. whereupon evolution of hydrogen chloride gas commenced and an oily layer separated. The mixture was refluxed for 2 hours and then allowed to cool. The solidified product was collected and dried under vacuum at 50° C. to give a waxy material; inherent viscosity 0.16 (0.5% in TFE at 30° C.); differential thermal analysis, Tg=−11° to −4° C., Tm=72° C.

EXAMPLE 11

1. Synthesis of poly[oxysuccinoyloxydodecane-1,12-di(amidocarbonylmethylene)-co-10%-oxysuccinoyloxy-4,9-dioxadodecane-1,12-di(amidocarbonylmethylene)].

Exactly 457.8 g (1.449 moles) of 1,12-di(hydroxyacetamido)dodecane prepared according to the procedure in Example 1 and 51.5 g (0.161 mole) of 1,12-di(hydroxyacetamido)-4,9-dioxadodecane prepared according to the procedure in Example 10 were placed in a 5 liter resin flask and 1.5 kg of chlorobenzene added. The reaction was conducted as described in Example 5. After distillation of approximately 200 ml of chlorobenzene, 249.5 g (1.610 moles) of redistilled succinyl chloride was added through an addition funnel to the rapidly stirring solution. Approximately 20 minutes after addition of succinyl chloride, the solution became viscous and the polymer soon solidified and separated from the solution. The mixture was refluxed with stirring for an additional 2 hours during which time the evolution of hydrogen chloride subsided. The product was collected by filtration and dried under vacuum at 100° C. to yield 524 g of powder; inherent viscosity 0.31 (0.5% in TFE at 30° C.); differential thermal analysis, Tg=+16° to +38° C., Tm=135° C.

The product was placed in a dish and heated in a vacuum oven for 6 days at 128° C. under partial vacuum. During this time a slow stream of dry nitrogen was passed over the polymer which remained in the solid state. As a result of this treatment the inherent viscosity increased significantly (0.48).

2. Fiber evaluation.

The above polymer was melt extruded and oriented as described in Example 1 to produce uniform fiber with a tenacity of 1.93 g/denier, 43% elongation, and modulus of 1.37 g/denier. This fiber is noticeably more flexible than the fiber prepared from homopolymer in Example 5.

EXAMPLE 12

Synthesis of poly[3-oxapentane-1,5-di(carbonyloxy)-dodecane-1,12-di(amidocarbonylmethylene)].

Anhydrous dioxane (250 ml) and 1,12-di(hydroxyacetamido)dodecane (46.9 g, 0.148 mole) prepared according to the procedure in Example 1 were placed in a 500 ml round bottom flask and heated under reflux with overhead mechanical stirring. Redistilled diglycoyl chloride (25.4 g, 0.148 mole) was added cautiously through an addition funnel to the refluxing solution. The hydrogen chloride gas which evolved was entrained in a stream of dry nitrogen and trapped in a water filled gas washing bottle. An oily layer soon separated from the solution and refluxing was continued for 4 hours. The mixture was then allowed to cool and the solidified material collected and dried under vacuum to give 67.4 g of product; inherent viscosity 0.23 (0.5% in TFE at 30° C.); differential thermal analysis, Tg=+19° to +53° C., Tm=124° C.

The polymer was placed in a U shaped tube and heated in an oil bath at 100° to 115° C. for 5 days. During this time a slow stream of dry nitrogen was passed through the polymer which remained in the solid state. As a result of this treatment the inherent viscosity increased significantly (0.34). Filaments pulled from the melted polymer were easily cold drawn by hand to give tenacious fiber.

EXAMPLE 13

1. Synthesis of 4,4'-methylenebis (α-hydroxypropiamidocyclohexane).

Molten 4,4'methylenebis(cyclohexylamine) (224.0 g, 1.065 moles) was placed in a 1 liter round bottom flask and 85% lactic acid (225.5 g, 2.13 moles) added slowly through an addition funnel with stirring and cooling. The resultant liquid was then heated in an oil bath to 190° C. whereupon distillation of water occurred. Heating was continued at 190° C. for 4 hours after which time distillation of water subsided and the liquid was poured into a Pyrex baking dish. Upon cooling the product solidified into a clear, amber colored glass. The solid was broken up and recrystallized twice from tetrahydrofuran containing 10% methanol to give lustrous, white flakes; m.p. 195°-199° C.; infrared (Nujol), 1640 cm$^{-1}$, 3300 cm$^{-1}$; proton nuclear magnetic resonance (DMSO-d$_6$/TMS, 100 MHz), δ0.6-1.5 (complex multiplet with doublet superimposed at δ1.15, 18 protons), δ1.5-1.8 (doublet, 8 protons), δ3.50 (broad singlet, 2 protons), δ3.7-4.1 (multiplet, 2 protons), δ5.35 (doublet, 2 protons), δ7.30 (doublet, 2 protons).

2. Synthesis of poly[oxysebacoyloxycyclohexane-1,4,-di(amidocarbonylethylidene)].

Exactly 86.0 g (0.2427 mole) of 4,4'-methylenebis (hydroxypropiamidocyclohexane) were placed in a 1 liter 3-neck round bottom flask and 600 ml of chlorobenzene added. The mixture was heated with overheated stirring and approximately 50 ml of chlorobenzene distilled. The solid remained undissolved and formed a thick suspension. Vacuum redistilled sebacoyl chloride (58.0 g, 0.2427 mole) was added carefully through an addition funnel with rapid stirring. This caused the diamidediol to dissolve and form a clear, colorless solution. The heating and stirring were continued for 45 min. during which time HCl evolved and the solution viscosity increased markedly. The solvent was then removed by distillation under reduced pressure and the resulting solid product kept under high vacuum overnight at 115° C. Upon cooling, the flask broke in numerous places. This polymer gave no adhesive failure with the glass flask which had to be removed by pulverization. The polymer is a hard, tough, colorless, thermoplastic solid which can be cold drawn to give strong, rigid filaments; inherent viscosity 1.17 (0.5% in TFE at 30° C.); differential thermal analysis, Tg= +90° to 100° C., Tm=199° C.

EXAMPLE 14

1. Synthesis of poly[oxysuccinoyloxydodecane-1,12-di(amidocarbonylmethylene)-co-10%-oxysuccinoyloxy-4,9-dioxadecane-1,12-di-(amidocarbonylmethylene)].

A ten gallon glass-lined reaction kettle equipped with a reflux condenser, pyrometer, addition funnel, and dry nitrogen purge was charged with exactly 1,942.4 g (6.15 moles) of 1,12-di(hydroxyacetamido)dodecane prepared according to the procedure in Example 1, 218.6 g (0.68 moles) of 1,12-di(hydroxyacetamido)-4,9-dioxadecane prepared according to the procedure in Example 10, and 6 gallons of chlorobenzene. The reaction kettle was heated by means of a steam jacket to 130° C. for 30 minutes with stirring to insure complete dissolution of the diamidediol monomers. The temperature was then stabilized at 125° C. and the stirring speed increased to the maximum setting. Exactly 1,058.6 g (6.83 moles) of vacuum redistilled succinyl chloride was added through the addition funnel at a constant rate during the time course of 3 minutes and 40 seconds. Stirring and heating were continued at 125° C. for 30 minutes after which time the stirring rate was decreased and the reactor allowed to cool to room temperature. The granular product was collected on a large ceramic filter, rinsed with heptane, and placed in a vacuum oven at 100° C. After drying for 2 days the inherent viscosity was 0.92 (0.5% in TFE at 30° C.) and increased to 1.03 after heating in the oven under partial vacuum and a slow stream of dry nitrogen for an additional 4 days at 120° C.

2. Fiber evaluation.

The above polymer was melt extruded and oriented as described in Example 1 to produce 2-0 suture size fiber with a tenacity of 6.53 g/denier, 34.8% elongation, and modulus of 20.6 g/denier. The number of throws for the interlacement of the parts to hold a surgeon's knot is two, the minimum possible number, and the knot strength is 47.5% of the tensile strength.

EXAMPLE 15

1. Synthesis of poly[oxysuccinoyloxydodecane 1,12-di(amidocarbonylmethylene)-co-10%-3-oxapentane-1,5-di(carbonyloxy)dodecane-1,12-di(amidocarbonylmethylene)].

A five gallon glass-lined reaction kettle equipped with a reflux condenser, pyrometer, addition funnel, and dry nitrogen purge was charged with exactly 1,165 g (3.67 moles) of 1,12-di(hydroxyacetamido)dodecane prepared according to the procedure in Example 1, and 3 gallons of chlorobenzene. The reaction kettle was heated by means of a steam jacket to 130° C. for 30 minutes with stirring to insure complete dissolution of the monomer. The stirring speed was then increased to the maximum setting and a mixture of exactly 63.3 g (0.37 moles) of vacuum redistilled diglycoyl chloride and 511.5 g (3.30 moles) of vacuum redistilled succinyl chloride added through the addition funnel during the time course of 6 minutes and 45 seconds. The reaction mixture was stirred and refluxed for an additional 2 hours after which time the stirring rate was decreased and the mixture allowed to cool to room temperature. The granular product was collected on a large ceramic filter, rinsed with tetrahydrofuran, and placed in a vacuum oven at 130° C. After heating the product at 130° C. under partial vacuum and a slow stream of dry nitrogen for 5 days, the inherent viscosity was 0.58 (0.5% in TFE at 30° C.).

2. Fiber evaluation.

The above polymer was melt extruded and oriented as in Example 1 to produce 2-0 suture size fiber with a tenacity of 4.11 g/denier, 26.8% elongation, and modulus of 20.5 g/denier. The knot strength was 58% of the tensile strength.

3. In vivo evaluation.

The above fiber was implanted in mice as described in Example 1. The strength loss results are shown in Table 3 and in the accompanying figure.

TABLE 3

| Days Post Implantation | Tensile Strength Retained |
|---|---|
| 7 | 89.7% |
| 14 | 83.9% |
| 28 | 79.4% |
| 49 | 38.2% |

At eight months post-implantation the encapsulated fiber was broken into small fragments, 1 to 4 mm in length. These fragments were extremely soft and partially absorbed. The implantation site in each of the mice showed no visible inflammation or other evidence of an adverse reaction toward the polymer.

EXAMPLE 16

1. Synthesis of poly[oxysuccinoyloxydodecane-1,12-di(amidocarbonylmethylene)-co-20%-oxysuccinoyloxy-4,9-dioxadodecane-1,12-di(amidocarbonylmethylene)].

This polymer was prepared under exactly the same conditions described in Example 14 using 1,264 g (4.00 moles) of 1,12-di(hydroxyacetamido)dodecane prepared according to the procedure in Example 1, 320 g (1.00 mole) of 1,12-di(hydroxyacetamido)-4,9-dioxadodecane prepared according to the procedure in Example 10, 775 g (5.00 moles) of vacuum redistilled succinyl chloride, and 3.5 gallons of chlorobenzene. The succinyl chloride was added during the time course of 5 minutes and 10 seconds and the product was dried for 2 days at 130° C. to give an inherent viscosity of 0.99 (0.5% in TFE at 30° C.).

2. Fiber Evaluation.

The above polymer was melt extruded and oriented as in Example 1 to produce 2-0 suture size fiber with a tenacity of 4.67 g/denier, 38.2% elongtion, and modulus of 18.0 g/denier. The knot strength was 64% of the tensile strength.

3. In vivo evaluation.

The above fiber was implanted in mice as described in Example 1. The strength loss results are shown in Table 4.

TABLE 4

| Days Post Implantation | Tensile Strength Retained |
|---|---|
| 7 | 89.2% |
| 14 | 87.4% |
| 28 | 76.6% |
| 49 | 57.3% |

At eight months post-implantation the encapsulated fiber was broken into small fragments, 1 to 2 mm in length. These fragments were extremely soft and partially absorbed. The implantation site in each of the mice showed no visible inflammation or other evidence of an adverse reaction toward the polymer.

EXAMPLE 17

1. Synthesis of poly[oxysuccinoyloxydodecane-1,12-di(amidocarbonylmethylene)].

This polymer was prepared under the same conditions described in Example 14 using 1,081.4 g (3.42 moles) of 1,12-di(hydroxyacetamido)dodecane prepared according to the procedure in Example 1, 530.4 g (3.42 moles) of vacuum redistilled succinyl chloride, and 3 gallons of chlorobenzene. The succinyl chloride was added during the time course of 15 minutes and 13 seconds and the product was dried for 7 days at 130° C. to give an inherent viscosity of 0.58 (0.5% in TFE at 30° C.).

2. Fiber evaluation.

The above polymer was melt extruded and oriented as in Example 1 to produce 2-0 suture size fiber with a tenacity of 5.03 g/denier, 31.0% elongation, and modulus of 22.0 g/denier. The knot strength was 50% of the tensile strength.

What is claimed is:

1. A body absorbable polymeric material comprising a plurality of units of the general formula:

in which $R^1$ is hydrogen or methyl;

$R^3$ and $R^5$ are identical or different and are selected from the group consisting of the following, which are linear or branched, alkylene, alkylene having 1 or 2 nonadjacent catenary oxygen or sulfur atoms, alkenylene, cycloalkylene and arylene; said members of the group having up to 25 carbon atoms in the cyclic compounds and from 2 to 25 carbon atoms in the non-cyclic compounds;

$R^2$ and $R^4$ are hydrogen or alkyl having 1 to 4 carbon atoms or $R^2$ and $R^4$ together are linear or branched alkylene having one to four carbons forming with N-$R^3$-N a heterocyclic group having 5 or 6 ring atoms; and a and b are independently zero or one.

2. The body absorbable polymeric material of claim 1 wherein a and b are zero and $R^5$ is ethylene.

3. The body absorbable polymeric material of claim 2 wherein $R^1$, $R^2$ and $R^4$ are hydrogen and $R^3$ is selected from at least one of the group consisting of 1,12-dodecamethylene and 1,12-(4,9-dioxadodecamethylene).

4. A body absorbable material comprising a polymer of the general formula:

in which $R^1$ is hydrogen or methyl;

$R^3$ and $R^5$ are identical or different and are selected from the group consisting of the following, which are linear or branched, alkylene, alkylene having 1 or 2 nonadjacent catenary oxygen or sulfur atoms, alkenylene, cycloalkylene and arylene; and having up to 25 carbon atoms in the cyclic compounds and from 2 to 25 carbon atoms in the non-cyclic compounds;

$R^2$ and $R^4$ are hydrogen or alkyl having 1 to 4 carbon atoms or $R^2$ and $R^4$ together are linear or branched alkylene having one to four carbons forming with N-$R^3$-N a heterocyclic group having 5 or 6 ring atoms; a and b are independently zero or one; and n having an average value from about 10 to about 100.

5. The body absorbable surgical material of claim 4 wherein n is from about 30 to about 50.

6. The body absorbable surgical material of claim 5 wherein said material is in the form of at least one filament.

7. The body absorbable surgical material of claim 6 wherein said filament is in the form of a suture.

8. A body absorbable polymeric material for implantation which is a condensation product of the process comprising the steps of:
   (a) reacting a diamine with lactic or glycolic acid to form a diamidediol;
   (b) reacting said diamidediol with a bischloroformate or a compound selected from the group consisting of dicarboxylic acids, methyl and ethyl esters of dicarboxylic acids, diacid chlorides and anhydrides of a dicarboxylic acid.

9. The body absorbable polymeric material of claim 8 wherein said diamine is 1,12-dodecanediamine.

10. The body absorbable polymeric material of claim 8 wherein said diamine is 4,9-dioxadodecane-1,12-diamine.

11. The body absorbable polymeric material of claim 8 wherein said diamidediol is selected from at least one of the group consisting of 1,12-di(hydroxyacetamido)-4,9-dioxadodecane and 1,12-di(hydroxyacetamido)dodecane.

12. The body absorbable polymeric material of claim 11 wherein said compound is succinyl chloride.

* * * * *

UNITED STATES PATENT AND TRADEMARK OFFICE
CERTIFICATE OF CORRECTION

PATENT NO. : 4,343,931

DATED : August 10, 1982

INVENTOR(S) : Thomas H. Barrows

It is certified that error appears in the above-identified patent and that said Letters Patent is hereby corrected as shown below:

Column 3, line 20, "cyclohexane-1,14-diamine" should read -- cyclohexane-1,4-diamine --.

Signed and Sealed this

Tenth Day of May 1983

[SEAL]

Attest:

GERALD J. MOSSINGHOFF

Attesting Officer

Commissioner of Patents and Trademarks